United States Patent
Fukuda

(10) Patent No.: US 10,043,294 B2
(45) Date of Patent: Aug. 7, 2018

(54) IMAGE PROCESSING DEVICE, RADIOGRAPHIC IMAGING SYSTEM, RECORDING MEDIUM STORING IMAGE PROCESSING PROGRAM, AND IMAGE PROCESSING METHOD

(71) Applicant: FUJIFILM CORPORATION, Minato-ku, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 306 days.

(21) Appl. No.: 14/732,790

(22) Filed: Jun. 8, 2015

(65) Prior Publication Data

US 2015/0302615 A1    Oct. 22, 2015

Related U.S. Application Data

(63) Continuation of application No. PCT/JP2013/083129, filed on Dec. 10, 2013.

(30) Foreign Application Priority Data

Dec. 14, 2012  (JP) ................................. 2012-273734
Nov. 22, 2013  (JP) ................................. 2013-242257

(51) Int. Cl.
*A61B 6/00*    (2006.01)
*G06T 11/00*    (2006.01)
(Continued)

(52) U.S. Cl.
CPC ............ *G06T 11/006* (2013.01); *A61B 6/025* (2013.01); *A61B 6/032* (2013.01); *A61B 6/502* (2013.01);
(Continued)

(58) Field of Classification Search
CPC ......... A61B 6/502; A61B 6/025; A61B 6/032; G01N 23/046; G01N 2223/419
See application file for complete search history.

(56) References Cited

U.S. PATENT DOCUMENTS

2007/0242868 A1* 10/2007 Stanton ................ G01N 23/046
                                                             382/131
2015/0036788 A1*  2/2015 Baba ..................... A61B 6/027
                                                              378/4

FOREIGN PATENT DOCUMENTS

JP          2005-7061 A       1/2005
JP         2005-152658 A      6/2005

* cited by examiner

*Primary Examiner* — Hoon Song
(74) *Attorney, Agent, or Firm* — Solaris Intellectual Property Group, PLLC

(57) ABSTRACT

An image processing device that includes: an acquiring section that acquires a plurality of projection images in which a subject between a radiation detector and a radiation applying unit has, as a result of the radiation applying unit being moved to thereby change an angle of incidence, with respect to the subject, of radiation applied from the radiation applying unit, been imaged at each different angle of incidence; a processing section that performs frequency processing that attenuates, relative to a high-frequency component, a low-frequency component of projection images in which the angle of incidence is equal to or greater than a first threshold; and a tomographic image generating section that generates tomographic images of the subject by image reconstruction from projection images in which the angle of incidence is less than the first threshold and from the frequency-processed projection images.

10 Claims, 14 Drawing Sheets

(51) Int. Cl.
*A61B 6/02* (2006.01)
*A61B 6/03* (2006.01)
(52) U.S. Cl.
CPC ............ *A61B 6/5205* (2013.01); *A61B 6/542* (2013.01); *G06T 2207/10004* (2013.01); *G06T 2207/10081* (2013.01)

RIGHT AND LEFT DIRECTION

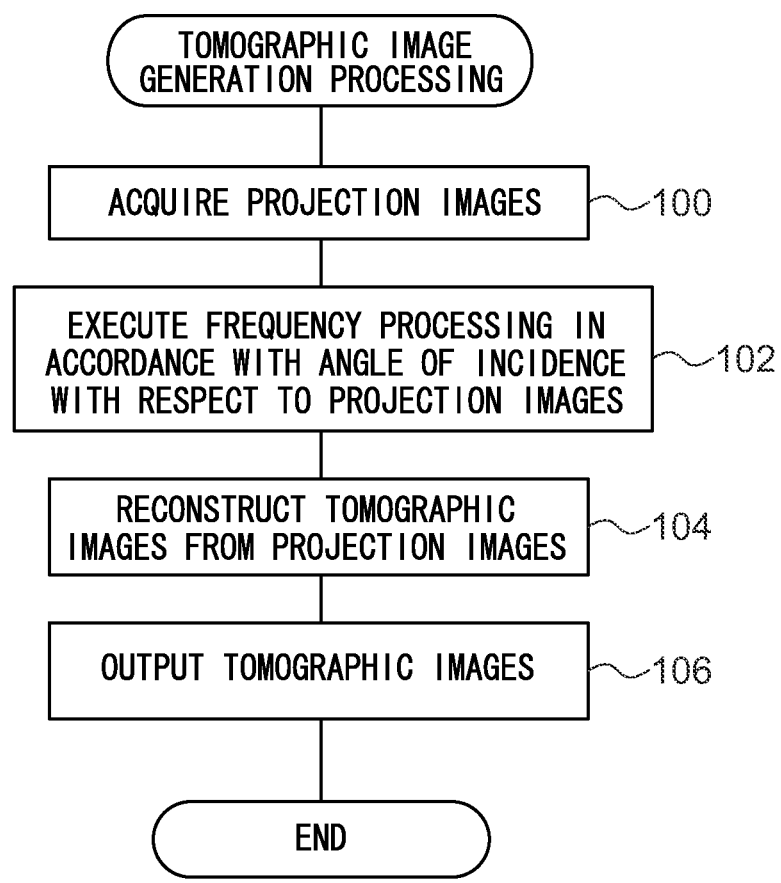

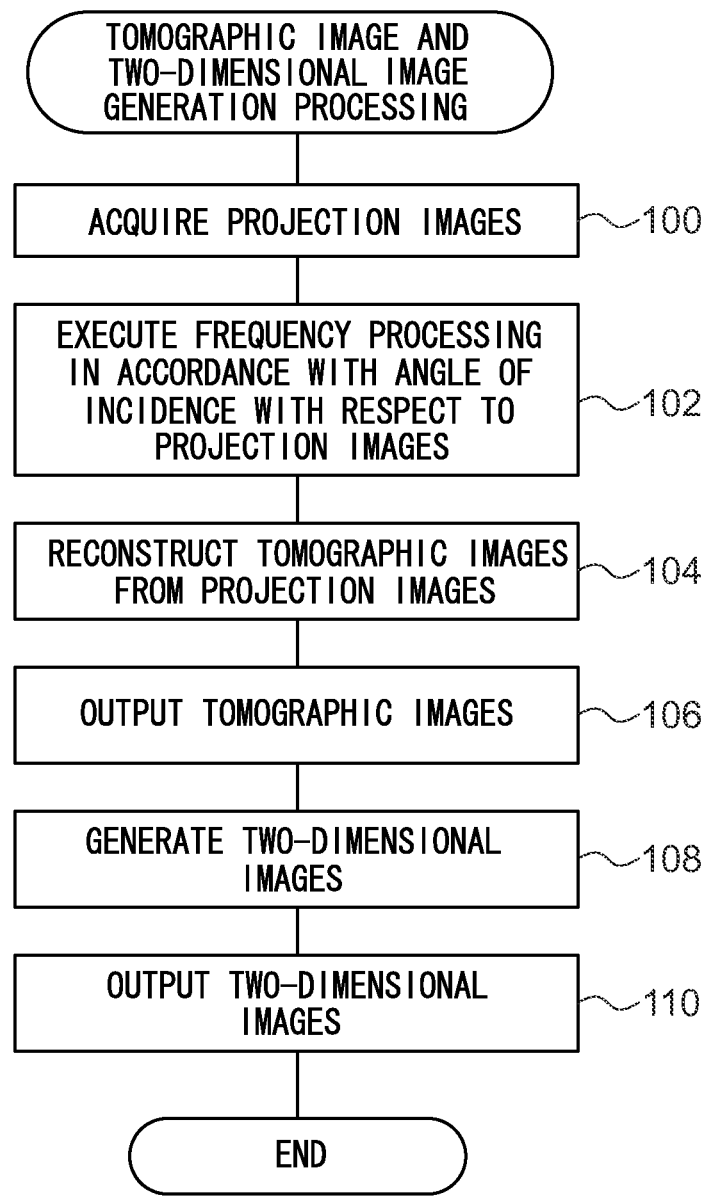

IMAGE PROCESSING DEVICE, RADIOGRAPHIC IMAGING SYSTEM, RECORDING MEDIUM STORING IMAGE PROCESSING PROGRAM, AND IMAGE PROCESSING METHOD

CROSS-REFERENCE TO RELATED APPLICATION

This application is a continuation application of International Application No. PCT/JP2013/083129, filed Dec. 10, 2013, the disclosure of which is incorporated herein by reference in its entirety. Further, this application claims priority from Japanese Patent Application No. 2012-273734, filed Dec. 14, 2012 and Japanese Patent Application No. 2013-242257, filed Nov. 22, 2013, the disclosures of which are incorporated herein by references in their entirety.

FIELD

The disclosure pertains to image processing devices, a radiographic imaging system, a recording medium storing a image processing program, and image processing methods, and particularly relates to image processing devices, a radiographic imaging system, a recording medium storing a image processing program, and image processing methods that generate tomographic images from radiographic images that have been captured by applying radiation at different angles to a subject.

BACKGROUND

Conventionally, radiographic imaging machines that perform radiographic imaging for the purpose of medical diagnosis have been known. An example of this type of radiographic imaging machine is a mammography machine that images the breasts of an examinee for the purpose of early detection of breast cancer. Furthermore, in connection with mammography machines, technologies that perform tomosynthesis imaging, in which radiation is applied at different angles to the breast of an examinee to image the breast, are known. In tomosynthesis imaging, tomographic images (substantially) parallel to the detection plane are generated at a predetermined slice width by reconstructing them from plural radiographic images (hereinafter called projection images) that have been captured by applying radiation to a subject while changing the angle of incidence of the radiation with respect to the detection plane.

However, in tomosynthesis imaging, the angles when applying the radiation are restricted, so even if the tomographic images are reconstructed by simply superimposing the projection images using the back-projection method, for example, sometimes a phantom image of an object ends up appearing in a region where that object is not really present. More specifically, sometimes, due to back-projection, a phantom image ends up appearing in a region where an object is not really present in a tomographic image at a slice position differing from a tomographic image at a slice position where the object is present. If the phantom image is too conspicuous, it becomes difficult to ascertain the object of interest. The same situation also occurs when using other methods to implement tomographic image reconstruction.

The filtered back-projection (FBP) method, which is a representative CT reconstruction method, can also be applied to reconstruct tomographic images by back-projecting them from projection images on which filtering has been uniformly performed. This can mitigate phantom images in the depth direction to a certain extent, but in the case of tomosynthesis imaging, if filtering is uniformly performed, sometimes the density of the subject image in the tomographic images ends up being quite different from what it is in the projection images.

On the other hand, in CT imaging, which compared to tomosynthesis imaging has no restrictions on the angles at which the radiation is applied, when tomographic images have been reconstructed using the FBP method that performs uniform filtering on each of the projection images and performs back-projection, the phantom images can be cancelled out when the projection images are superimposed on top of one another during back-projection, and phantom images (artifacts) on the tomographic images that are reconstructed are controlled. Consequently, the situation described above is a problem unique to tomosynthesis imaging.

As a technology for controlling artifacts in tomosynthesis imaging, a method comprising identifying a plurality of non-uniform weighting factors for use in back-projection processing and back-projecting image data by application of the non-uniform weighting factors is known (e.g., see JP-A No. 2005-152658). Furthermore, although it does not involve tomosynthesis imaging, an image processing device that performs image processing on the basis of the angle of incidence of radiation as correction processing with respect to a radiographic image obtained by ordinary two-dimensional imaging (ordinary imaging in which the radiation is applied to the subject from a fixed position without moving the radiation source) is also known (e.g., see JP-A No. 2005-7061).

SUMMARY

An aspect of the disclosure is an image processing device, includes: an acquiring section that acquires a plurality of projection images in which a subject between a radiation detector and a radiation applying unit has, as a result of the radiation applying unit being moved to thereby change an angle of incidence, with respect to the subject, of radiation applied from the radiation applying unit, been imaged at each different angle of incidence; a processing section that performs frequency processing that attenuates, relative to a high-frequency component, a low-frequency component of projection images in which the angle of incidence is equal to or greater than a first threshold; and a tomographic image generating section that generates tomographic images of the subject by image reconstruction from projection images in which the angle of incidence is less than the first threshold and from the frequency-processed projection images.

BRIEF DESCRIPTION OF DRAWINGS

FIG. 5 is a flowchart showing a flow of a tomographic image generation processing program;

FIG. 10 is a flowchart showing a flow of a tomographic image and two-dimensional image generation processing program;

DETAILED DESCRIPTION OF THE INVENTION

An embodiment of the present disclosure will be described in detail below with reference to the drawings. This embodiment is not intended to limit the present disclosure.

Figure 1:
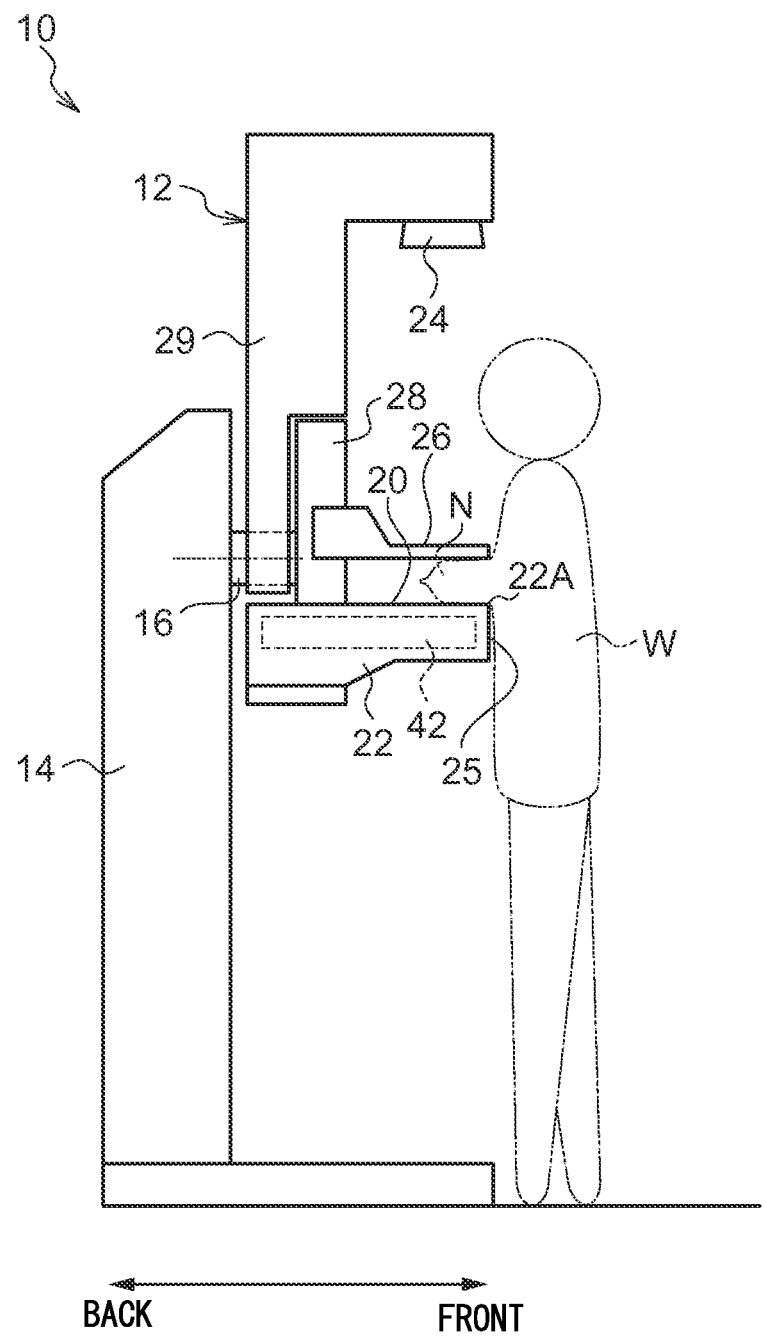
FIG. 1 is a plan view showing an example of the configuration of a radiographic imaging machine of an embodiment.
Figure 2:
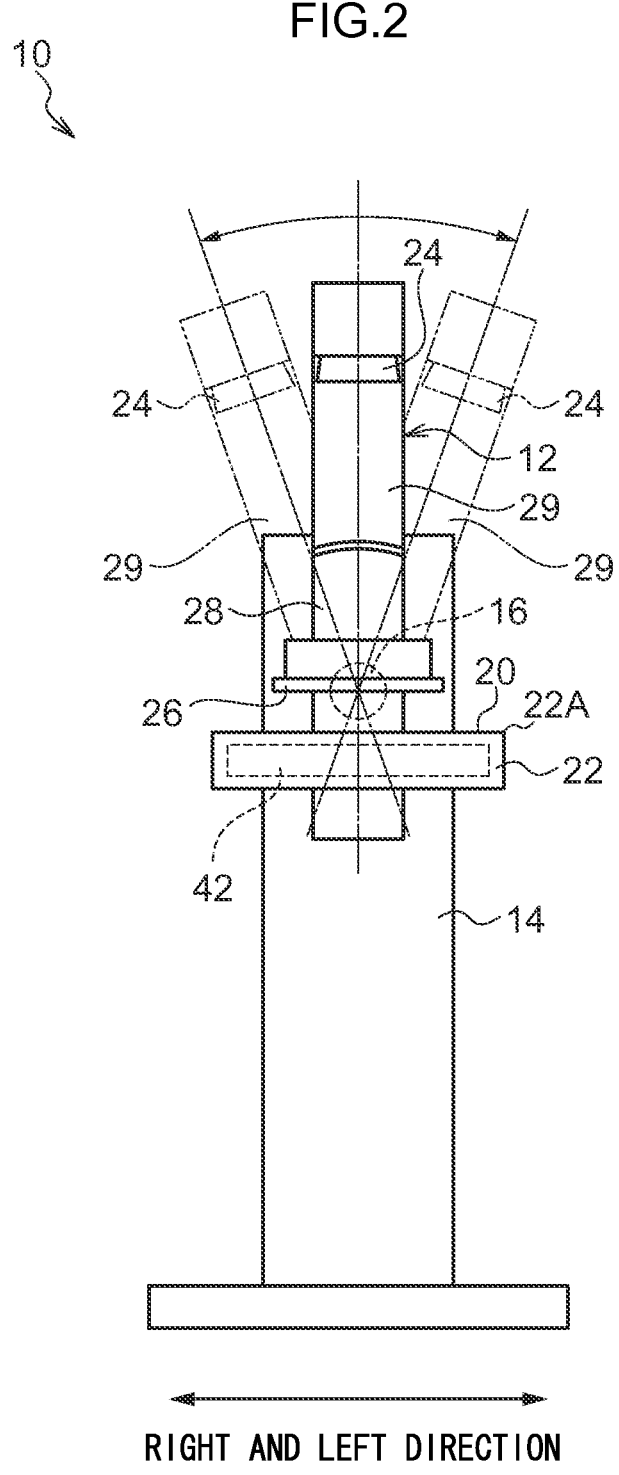
FIG. 2 is a drawing showing an example of the configuration of the radiographic imaging machine of the embodiment during imaging.
Figure 3:
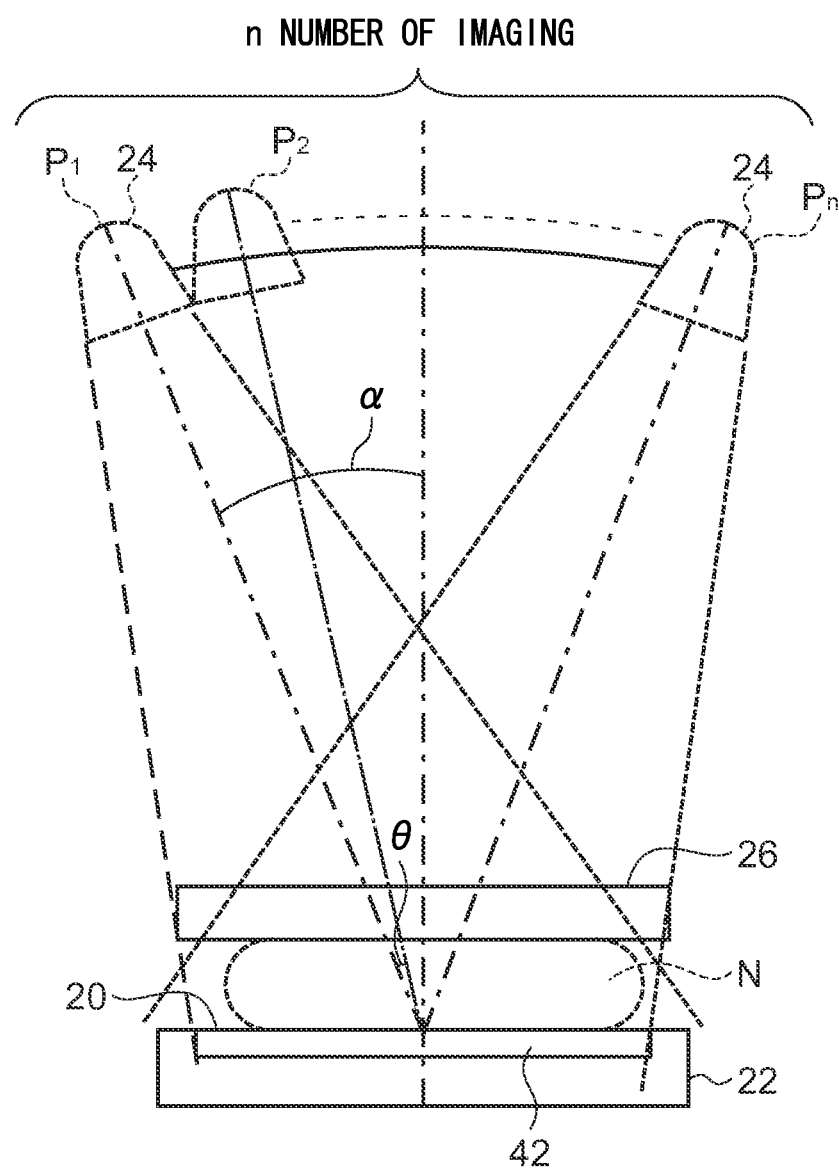
FIG. 3 is an explanatory drawing for describing the radiographic imaging machine of the embodiment during imaging.

As shown in FIG. 1 to FIG. 3, a radiographic imaging machine 10 of the present embodiment is a machine that uses radiation (e.g., X-rays) to image breasts N of an examinee W in an upright state in which the examinee W is standing, and the radiographic imaging machine 10 is, for example, called a mammography machine. In what follows, description will be given by referring to the near side of the radiographic imaging machine 10 that is near the examinee W when the examinee W is facing the radiographic imaging machine 10 during imaging as the machine front side of the radiographic imaging machine 10, referring to the far side of the radiographic imaging machine 10 that is away from the examinee W when the examinee W is facing the radiographic imaging machine 10 as the machine back side of the radiographic imaging machine 10, and referring to the right and left direction of the examinee W when the examinee W is facing the radiographic imaging machine 10 as the machine right and left direction of the radiographic imaging machine 10 (see the arrows in FIG. 1 and FIG. 2).

Furthermore, the imaging target of the radiographic imaging machine 10 is not limited to the breasts N and may also, for example, be another region of the body or an object. Furthermore, the radiographic imaging machine 10 may also be a machine that images the breasts N of the examinee W in a seated state in which the examinee W is seated in a chair (including a wheelchair); it suffices for the radiographic imaging machine 10 to be a machine that can separately image the right and left breasts N of the examinee W at least in a state in which the upper body of the examinee W is upright.

As shown in FIG. 1, the radiographic imaging machine 10 is equipped with a measurement section 12, which is substantially C-shaped as seen in a side view and is disposed on the machine front side, and a base section 14, which supports the measurement section 12 from the machine back side.

The measurement section 12 is configured to have an imaging table 22 on which is formed a flat imaging table surface 20 with which the breast N of the examinee W in the upright state comes into contact, a compression plate 26 for compressing the breast N between it and the imaging table surface 20 of the imaging table 22, and a holding member 28 that supports the imaging table 22 and the compression plate 26. A member that allows radiation to pass through it is used for the compression plate 26.

Furthermore, the measurement section 12 is equipped with a radiation applying unit 24, in which a radiation source 30 (see FIG. 4) such as a tube is disposed and which applies radiation for examination from the radiation source 30 toward the imaging table surface 20, and a support member 29, which is separate from the holding member 28 and supports the radiation applying unit 24.

A rotating shaft 16 rotatably supported in the base section 14 is disposed in the measurement section 12. The rotating shaft 16 is fixed relative to the support member 29, so that the rotating shaft 16 and the support member 29 integrally rotate.

The rotating shaft 16 can be switched between a state in which it is coupled to and rotates integrally with the holding member 28 and a state in which it is decoupled from the holding member 28 and idles. Specifically, gears are disposed in the rotating shaft 16 and the holding member 28, and the gears are switched between a state in which they are engaged with one another and a state in which they disengaged from one another.

A variety of machine elements can be used to switch between transmitting and not transmitting the rotational force of the rotating shaft 16.

The holding member 28 supports the imaging table 22 and the radiation applying unit 24 in such a way that a predetermined distance is maintained between the imaging table surface 20 and the radiation applying unit 24 and slidably holds the compression plate 26 in such a way that the distance between the compression plate 26 and the imaging table surface 20 can be changed.

The imaging table surface 20 with which the breast N comes into contact is formed of carbon, for example, from the standpoint of radiation transmissivity and strength. A radiation detector 42, to which the radiation passing through the breast N and the imaging table surface 20 is applied and which detects that radiation, is disposed inside the imaging table 22. The radiation detected by the radiation detector 42 is visualized and thus a radiographic image is generated.

The radiographic imaging machine 10 of the present embodiment is a machine that can apply radiation, while changing (varying) the angle of incidence of the radiation with respect to the detection plane of the radiation detector 42, to the breast N serving as the subject to thereby perform imaging at each different angle of incidence. Here, "angle of incidence" means the angle formed by the normal to the detection plane of the radiation detector 42 and the radiation axis. Furthermore, here, the detection plane of the radiation detector 42 is a plane substantially parallel to the imaging table surface 20.

FIG. 2 and FIG. 3 show the posture of the radiographic imaging machine 10 during imaging and the positions of the radiation applying unit 24 during imaging. As shown in FIG. 2 and FIG. 3, the radiographic imaging machine 10 performs imaging while tilting the support member 29, which supports the radiation applying unit 24 and also supports, via the holding member 28, the imaging table 22.

When, as shown in FIG. 3, the radiographic imaging machine 10 performs imaging by applying radiation, while changing the angle of incidence of the radiation with respect to the detection plane of the radiation detector 42 in a predetermined range (e.g., a range of ±20 degrees relative to the normal to the detection plane), to the breast N (hereinafter this imaging will be called tomosynthesis imaging), the rotating shaft 16 idles relative to the holding member 28, the imaging table 22 and the compression plate 26 do not move, and the support member 29 rotates, so that only the radiation applying unit 24 moves in a circular arc. In the present embodiment, the position of the radiation applying unit 24 is moved a predetermined angle θ at a time from angle α as shown in FIG. 3, so that imaging is performed at n number of places in which the position of the radiation applying unit 24 changes from P1 to Pn. Hereinafter, the angle of incidence of the radiation with respect to the direction of the normal to the detection plane of the radiation detector 42 will simply be called "angle of incidence".

Usually when performing tomosynthesis imaging, radiation is applied n number of times to each breast N of the subject W, so in order to keep the amount of radiation to which the examinee W is exposed from increasing, the dose of radiation applied during each exposure is reduced and the radiation is applied in such a way that, for example, in a total of n number of exposures, the dose of radiation becomes about the same as the dose of radiation applied during ordinary two-dimensional imaging (ordinary imaging in which the radiation is applied to the subject from a fixed position without moving the radiation source 30).

Furthermore, the radiographic imaging machine 10 of the present embodiment is a machine that can perform both craniocaudal (CC) imaging and mediolateral oblique (MLO) imaging of the breasts N. During CC imaging, the posture of the holding member 28 is adjusted so that the imaging table surface 20 is face up and the posture of the support member 29 is adjusted so that the radiation applying unit 24 is positioned over the imaging table surface 20. Because of this, CC imaging is performed by applying, from the head toward the feet of the upright subject W, the radiation from the radiation applying unit 24 to the breast N. Furthermore, during MLO imaging, usually the posture of the holding member 28 is adjusted so that the imaging table 22 is rotated from 45° to less than 90° compared to during CC imaging and the examinee W is positioned so that the armpit of the examinee W is up against a side wall corner portion 22A on the machine front side of the imaging table 22. Because of this, MLO imaging is performed by applying, from the axial center side of the torso of the examinee W outward, the radiation from the radiation applying unit 24 to the breast N.

A chest wall surface 25, with which the chest region below the breasts N of the examinee W is brought into contact during imaging, is formed on the surface on the machine front side of the imaging table 22. The chest wall surface 25 is flat.

In this connection, as mentioned above, in the radiographic imaging machine 10 of the present embodiment, the breast N is brought into contact with the imaging table surface 20 of the imaging table 22 and is compressed and immobilized by the compression plate 26. For this reason, in the radiographic imaging machine 10 of the present embodiment, the angle of incidence of the radiation with respect to the direction of the normal to the detection plane of the radiation detector 42, which is a plane parallel to the imaging table surface 20, and the angle of incidence of the radiation with respect to the breast N become equal. Here, the "angle of incidence of the radiation with respect to the breast N" means the angle formed by the direction of gravity and a straight line joining a predetermined point inside the breast N (e.g., the center point of the section of the breast N in contact with the imaging table surface 20) and the radiation source 30.

Figure 4:
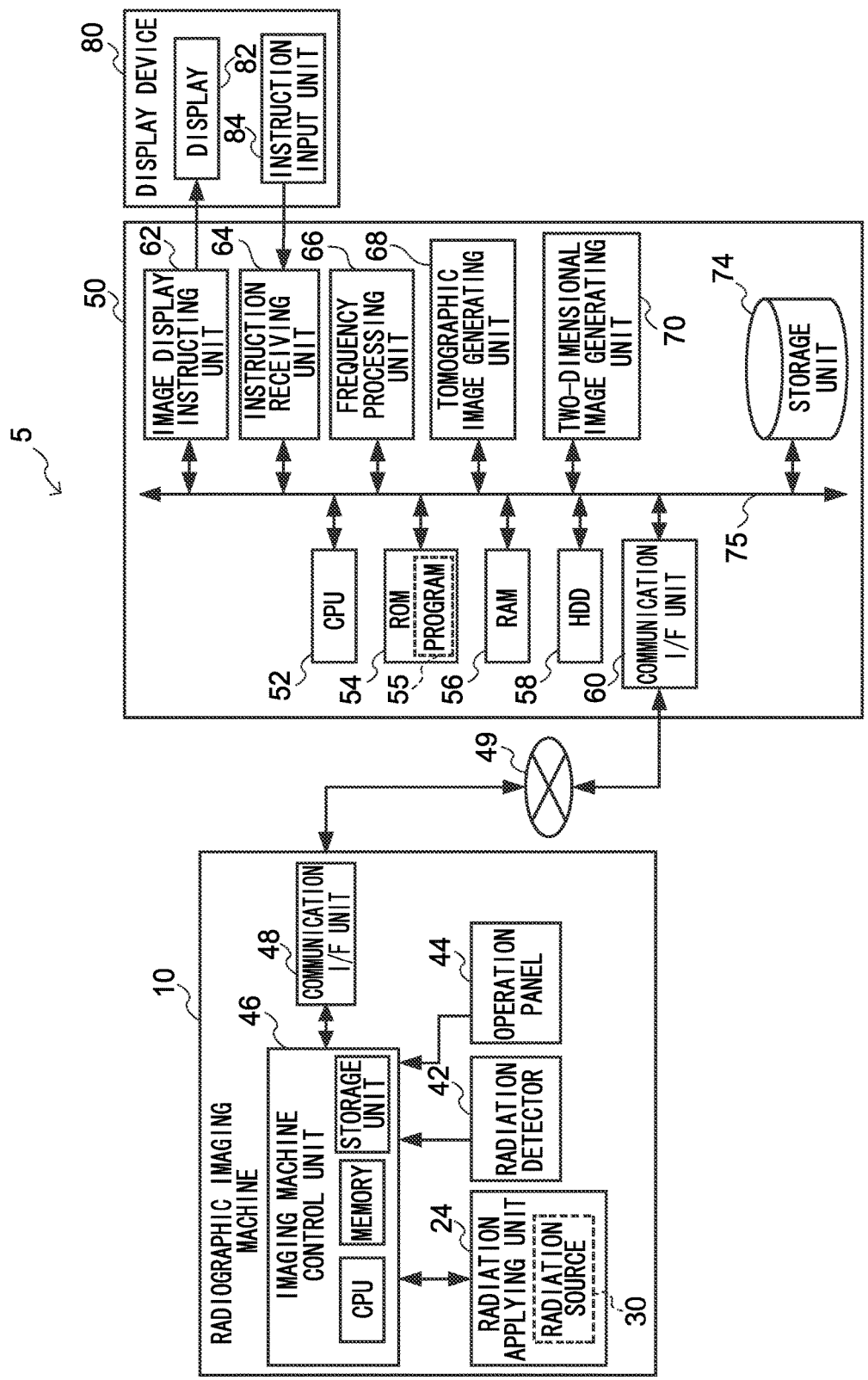
FIG. 4 is a block diagram showing an example of the configuration of a radiographic imaging system of the embodiment.

FIG. 4 shows a block diagram of an example of the configuration of a radiographic imaging system 5 of the present embodiment.

The radiographic imaging system 5 of the present embodiment is configured to have the radiographic imaging machine 10, an image processing device 50, and a display device 80.

The radiographic imaging machine 10 is configured to include the radiation applying unit 24, the radiation detector 42, an operation panel 44, an imaging machine control unit 46, and a communication I/F unit 48.

The imaging machine control unit 46 has the function of controlling the operations of the entire radiographic imaging machine 10 and is configured to have a central processing unit (CPU), a memory including a read-only memory (ROM) and a random access memory (RAM), and a nonvolatile storage unit comprising a hard disk drive (HDD) and/or a flash memory. Furthermore, the imaging machine control unit 46 is connected to the radiation applying unit 24, the radiation detector 42, the operation panel 44, and the communication I/F unit 48.

When an instruction to apply radiation is received from an operator by the operation panel 44 (exposure switch), the imaging machine control unit 46 causes radiation to be applied from the radiation source 30 disposed in the radiation applying unit 24 to the imaging table surface 20 in accordance with an imaging menu (details described later) that has been set on the basis of designated exposure conditions. In the present embodiment, the radiation source 30 applies cone beam radiation (e.g., a conical X-ray beam).

The radiation detector 42 is irradiated with the radiation, which carries image information, records the image information, and outputs the recorded image information; for example, the radiation detector 42 is configured as a flat panel detector (FPD) in which a radiation-sensitive layer is disposed and which converts the radiation to digital data and outputs the digital data. The radiation-sensitive layer can be disposed substantially parallel to the imaging table surface 20. When the radiation detector 42 is irradiated with the radiation, the radiation detector 42 outputs to the imaging machine control unit 46 the image information representing a radiographic image. In the present embodiment, the radiation detector 42 is irradiated with the radiation passing through the breast N to obtain image information representing a radiographic image.

The operation panel 44 has the function of allowing the setting of various types of operation information including imaging conditions and various types of operation instructions.

The imaging conditions set at the operation panel 44 include exposure conditions, which include tube voltage, tube current, and duration of application, and information such as posture information. The posture information designated at the operation panel 44 includes information representing imaging positions (including angles of incidence) when performing imaging by making the radiation incident at multiple angles of incidence on the breast N.

These exposure conditions, the various types of operation information such as the posture information, and the various types of operation instructions may be set by an operator using the operation panel 44, or may be obtained from another control device (a radiology information system, or RIS, which is a system that manages information, such as medical examinations and medical diagnoses using radiation), or may be stored beforehand in a storage unit.

When the various types of information are set from the operation panel 44, the imaging machine control unit 46 executes radiographic imaging by causing radiation to be applied from the radiation applying unit 24 to the imaging region (the breast N) of the examinee W in accordance with the imaging menu that has been set on the basis of the various types of information that have been set. When performing tomosynthesis imaging of the breast N, the imaging machine control unit 46 adjusts the posture of the holding member 28 so that the imaging table surface 20 is face up and adjusts the posture of the support member 29 so that the radiation applying unit 24 is positioned over the imaging table surface 20. Then, as shown in FIG. 3, on the basis of the imaging conditions, the imaging machine control unit 46 rotates the support member 29 to thereby move the radiation applying unit 24 the angle θ at a time from angle α in a circular arc and causes radiation to be applied from the radiation source 30 disposed in the radiation applying unit 24. Because of this, n number of radiographic images, in which the angles of incidence of the radiation are different from one another, are obtained.

The communication I/F unit 48 is a communication interface having the function of sending and receiving, via a network 49, captured radiographic images and various types of information between the radiographic imaging machine 10 and the image processing device 50.

The image processing device 50 has the function of generating tomographic images reconstructed from the radiographic images acquired from the radiographic imaging machine 10 and has the function of performing, with respect to the radiographic images, image processing for allowing a doctor to study an object of interest such as a mass. Hereinafter, the person—such as a doctor—who studies the captured radiographic images and generated tomographic images and performs the diagnosis of tumors and so forth will be called a user, and the radiographic images obtained as a result of the radiation detector 42 detecting the radiation by tomosynthesis imaging in the radiographic imaging machine 10 will called "projection images".

The image processing device 50 is configured to have a CPU 52, a ROM 54, a RAM 56, a HDD 58, a communication I/F unit 60, an image display instructing unit 62, an instruction receiving unit 64, a frequency processing unit 66, a tomographic image generating unit 68, a two-dimensional image generating unit 70, and a storage unit 74. These are connected to one another via a bus 75 such as a control bus or a data bus so that they can send and receive information to and from one another.

The CPU 52 controls the entire image processing device 50; specifically, the CPU 52 performs control by executing a program 55 stored in the ROM 54 (including programs for executing tomographic image generation processing and tomographic image and two-dimensional image generation processing described later). Although in the present embodiment the program 55 is stored beforehand, the program 55 is not limited to this and may also be stored in a recording medium such as a CD-ROM or a removable disk and installed in the ROM 54 from the recording medium, or the program 55 may also be installed in the ROM 54 from an external device via a communication line such as the Internet. The RAM 56 secures a region for work when the CPU 52 executes the program 55. The HDD 58 stores and retains various types of data.

The communication I/F unit 60 is a communication interface having the function of sending and receiving, via the network 49, captured radiographic images and various types of information between the image processing device 50 and the radiographic imaging machine 10.

The image display instructing unit 62 has the function of instructing a display 82 of the display device 80 to display radiographic images.

The display device 80 of the present embodiment has the function of displaying captured radiographic images and is configured to have the display 82 on which the radiographic images are displayed and an instruction input unit 84. The instruction input unit 84 may, for example, be a touch display and/or a keyboard and a mouse. Using the instruction input unit 84, the user (e.g., a doctor) can input instructions related to the display of radiographic images. The instruction receiving unit 64 has the function of receiving the instructions from the user that have been input using the instruction input unit 84 of the display device 80.

The frequency processing unit 66 performs frequency processing in accordance with the angles of incidence when the projection images were captured. More specifically, the frequency processing unit 66 performs frequency processing that attenuates, relative to a high-frequency component, a low-frequency component of the projection images in which the angle of incidence is equal to or greater than a threshold (hereinafter called a first threshold). The value of the first threshold is set beforehand.

In the present embodiment, the range of spatial frequencies in which an object larger than the size of an object of interest serving as the target of reading by the user is included is regarded as a low-frequency region, and an object included in that low-frequency region is regarded as the low-frequency component. Furthermore, in the present embodiment, the range of spatial frequencies higher than the upper limit of the low-frequency region is regarded as a high-frequency region, and an object included in that high-frequency region is regarded as the high-frequency component. Moreover, in the present embodiment, the typical size of a calcification (e.g., 300 μm) is applied as the size of the object of interest, but the size of the object of interest is not limited to this, and the size of another object of interest such as a mass, for example, may also be applied.

Here, the frequency processing unit 66 of the present embodiment performs, as the frequency processing, frequency processing that attenuates, relative to the high-frequency component and in accordance with an enhancement factor indicating the degree of enhancement, the low-frequency component of the projection images in which the angle of incidence is equal to or greater than the first threshold. Furthermore, in the frequency processing unit 66 of the present embodiment, the larger the enhancement factor becomes beyond a predetermined threshold (in the present embodiment, 1.0), the greater the degree to which the frequency processing unit 66 enhances the frequency component in the range of spatial frequencies serving as the processing target becomes, and the smaller the enhancement factor becomes below that threshold, the greater the degree to which the frequency processing unit 66 attenuates that frequency component becomes.

As the frequency processing, the technology disclosed in JP-A No. H10-63838, for example, can be applied. Specifically, the frequency processing unit 66 first performs, with respect to the projection images, processing that changes the degree to which it lowers the sharpnesses of the images and lowers the sharpnesses to thereby generate plural images (hereinafter called "unsharp images") whose sharpnesses are lower than those of the projection images and whose sharpnesses are different from one another. Although in the present embodiment filtering using a Gaussian filter is applied as the processing that lowers the sharpnesses, the processing that lowers the sharpnesses is not limited to this, and other known methods such as filtering using a moving average filter, for example, may also be applied.

Next, the frequency processing unit 66 uses the projection images and the unsharp images to perform a conversion according to a predetermined conversion function with respect to each of the differences between the images whose sharpnesses are the closest and also generate images in which the differences after the conversion are integrated. Then, the frequency processing unit 66 generates, as images on which the frequency processing has been performed, images in which the projection images and the images on which has been performed the processing of enhancement and attenuation in accordance with the preset enhancement factor have been added to the images obtained by the integration.

Here, the enhancement factor and the range of spatial frequencies applied when the frequency processing unit 66 performs the frequency processing with respect to the projection images may be stored beforehand in a storage unit such as the ROM 54, or may be input by the user via the instruction input unit 84, or may be input by an external device via the communication I/F unit 60. The above frequency processing is conventionally known art, so a more detailed description than given here will be omitted.

The tomographic image generating unit 68 has the function of generating tomographic images parallel to the imaging table surface 20 at a predetermined slice width by reconstructing them from the projection images in which the angle of incidence is less than the first threshold and the projection images that have been frequency-processed by the frequency processing unit 66. Although "parallel" is used in the present embodiment, this also includes substantially parallel.

The tomographic image generating unit 68 generates tomographic images at a predetermined slice width from the plural projection images that have been captured by moving the radiation applying unit 24 (the radiation source 30) to the positions of P1, P2, P3, . . . , Pn. The position at which an object of interest is projected onto a radiographic image differs depending on the angle of incidence of the radiation with respect to the imaging table surface 20. Therefore, the tomographic image generating unit 68 acquires from the radiographic imaging machine 10 the imaging conditions when the radiographic images were captured, calculates how much the object of interest moves between the plural radiographic images on the basis of the angles of incidence of the radiation included in the imaging conditions, and reconstructs the tomographic images on the basis of a known reconstruction method, such as the shift-and-add method.

As the reconstruction method, conventionally known CT reconstruction methods can also be used in addition to the shift-and-add method. For example, the filtered back-projection (FBP) method, which is a representative CT reconstruction method, can be used. FBP is a reconstruction method in which the filtered back-projection method is expanded taking parallel planar tomographic scans in tomographic imaging as part of a computer CT scan. Furthermore, the iterative reconstruction method described in JP-A No. 2011-125698 can also be used. This iterative reconstruction method is a reconstruction method for CT, but like the FBP method it can also be applied to reconstruction in the case of tomosynthesis imaging.

No matter which reconstruction method is used, add processing such as shift-and-add or back projection is performed to reconstruct the tomographic images after performing the frequency processing on the projection images for which the frequency processing is necessary.

The two-dimensional image generating unit 70 generates two-dimensional images by performing projection processing along a predetermined direction with respect to stacked images (a three-dimensional image) in which the plural tomographic images generated by the tomographic image generating unit 68 have been stacked or by performing add processing that adds corresponding pixel values along a predetermined direction.

The two-dimensional images generated by the two-dimensional image generating unit 70 will be briefly described. Although tomosynthesis imaging is becoming widely accepted in mammography diagnostics, the tomographic images obtained by tomosynthesis imaging are oftentimes used in mapping with the function of assisting the radiographic images obtained by the aforementioned two-dimensional imaging. Reasons for this include the fact that doctors are used to looking at radiographic images captured by ordinary two-dimensional imaging, the radiographic images are different in density from tomographic images, and the entirety can be grasped at once.

Consequently, conventionally there have been many instances where a diagnosis is made by performing two-dimensional imaging and also performing tomosynthesis imaging and combining the radiographic images acquired by two-dimensional imaging and the tomographic images acquired by tomosynthesis imaging.

However, the imaging dose and imaging time can be significantly reduced if images corresponding to radiographic images obtained by ordinary two-dimensional imaging can also be obtained by tomosynthesis imaging only. Therefore, in the present embodiment, the two-dimensional image generating unit 70 is disposed in the image processing device 50 in order to generate two-dimensional images corresponding to radiographic images captured by two-dimensional imaging from the plural tomographic images generated by tomosynthesis imaging.

The two-dimensional image generating unit 70 may also be configured to operate when the generation of two-dimensional images has been instructed by the instruction input unit 84. Furthermore, the image processing device 50 can also be given a configuration in which the two-dimensional image generating unit 70 is not disposed.

Furthermore, the frequency processing unit 66, the tomographic image generating unit 68, and the two-dimensional image generating unit 70 can each be realized by hardware such as, for example, hardware configured by a common electronic circuit or an application-specific integrated circuit (ASIC) or a field-programmable gate array (FPGA).

The storage unit 74 has the function of storing the image information representing the projection images captured by the radiographic imaging machine 10, the tomographic images generated by the tomographic image generating unit 68, and the two-dimensional images generated by the two-dimensional image generating unit 70; the storage unit 74 is, for example, a large-capacity storage device such as a hard disk. Furthermore, in the present embodiment, the imaging conditions (e.g., the angles of incidence of the radiation) when radiographic imaging was performed by the radiographic imaging machine 10 are also stored in the storage unit 74.

Next, the action of the radiographic imaging system 5 of the present embodiment will be described with reference to the drawings. First, a case will be described where the two-dimensional image generating unit 70 is not operated due to an instruction from the user.

When performing radiographic imaging, the radiographic imaging machine 10 executes, when an imaging menu is set, imaging in accordance with the imaging menu.

When an imaging instruction to perform tomosynthesis imaging has been input, as shown in FIG. 2, the radiographic imaging machine 10 adjusts the posture of the holding member 28 so that the imaging table surface 20 is face up and adjusts the support member 29 so that the radiation applying unit 24 is positioned over the imaging table surface 20.

The examinee W brings a breast N into contact with the imaging table surface 20 of the radiographic imaging machine 10. When an operation instruction to start compression is given to the operation panel 44 from the operator in this state, the compression plate 26 of the radiographic imaging machine 10 moves toward the imaging table surface 20.

When an imaging instruction to perform tomosynthesis imaging has been input to the operation panel 44 in this state, as shown in FIG. 3, the radiographic imaging machine 10 pertaining to the present embodiment rotates only the support member 29 to thereby move the radiation applying unit 24 the angle $\theta$ at a time from the angle $\alpha$ in a circular arc and applies the radiation on the basis of the imaging conditions at n number of places in which the position of the radiation applying unit 24 changes from P1 to Pn. The radiation beams individually applied from the radiation applying unit 24 pass through the breast N and thereafter reach the radiation detector 42.

When the radiation is applied, the radiation detector 42 outputs to the imaging machine control unit 46 sets of image information representing the projection images obtained by the applied radiation. When, as described above, the radiation is applied at n number of places in which the position of the radiation applying unit 24 changes from P1 to Pn, the radiation detector 42 outputs to the imaging machine control unit 46 sets of image information corresponding to n number of projection images.

The imaging machine control unit 46 outputs to the image processing device 50 each of the sets of image information that have been input. When, as described above, the radiation is applied at n number of places in which the position of the radiation applying unit 24 changes from P1 to Pn, the CPU of the imaging machine control unit 46 outputs to the image processing device 50 sets of image information corresponding to n number of projection images.

The image processing device 50 performs tomographic image generation processing in which it implements frequency processing on the projection images and thereafter reconstructs the tomographic images and causes the display device 80 to display them.

FIG. 5 is a flowchart showing a flow of a tomographic image generation processing program executed by the CPU 52 of the image processing device 50 of the present embodiment.

In step 100, the CPU 52 acquires the sets of image information corresponding to the plural (here, n number of) tomographic images from the radiographic imaging machine 10.

In step 102, the CPU 52 controls the frequency processing unit 66 to execute frequency processing according to the angles of incidence. As mentioned above, the frequency processing unit 66 performs frequency processing that attenuates, relative to the high-frequency component, the low-frequency component of the projection images in which the angle of incidence at the time of imaging is equal to or greater than the first threshold. Here, as an example of the frequency processing that attenuates the low-frequency component relative to the high-frequency component, by setting the enhancement factor with respect to the high-frequency component to 1.0 and setting the enhancement factor with respect to the low-frequency component to less than 1.0, the frequency processing unit 66 does not perform processing that enhances the high-frequency component but performs processing that attenuates the low-frequency component (hereinafter called low-frequency component attenuation processing). The frequency processing unit 66 does not perform the low-frequency component attenuation processing on the projection images in which the angle of incidence is less than the first threshold (the degree of attenuation of the low-frequency component is set to 0).

Furthermore, for the enhancement factor used here, a value obtained beforehand, by an experiment using a real version of the radiographic imaging machine 10 or by a computer simulation based on the design specifications of the radiographic imaging machine 10, as a value with which an object of interest serving as a reading target can be seen when a tomographic image obtained as a result has been read in accordance with the size of the object of interest can be applied.

Here, the processing performed by the frequency processing unit 66 will be described in detail.

Figure 6A:
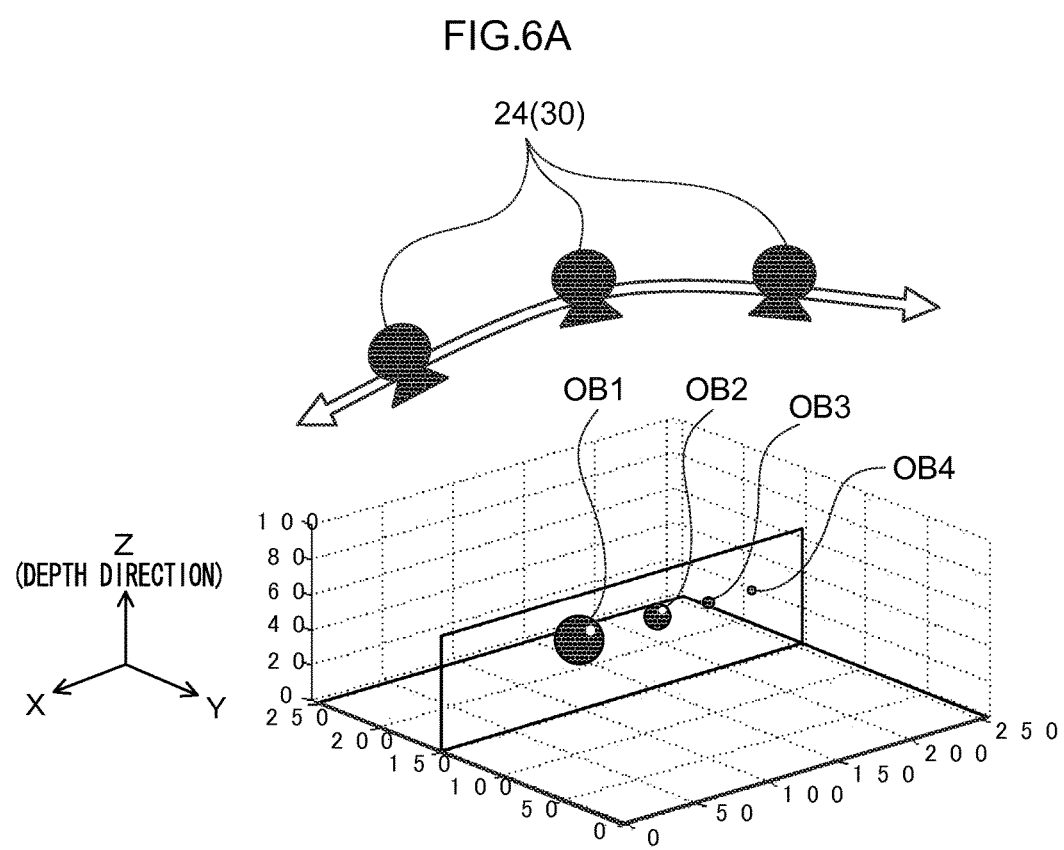
FIG. 6A is a drawing schematically showing an example of tomosynthesis imaging.

FIG. 6A is a drawing schematically showing an example of tomosynthesis imaging. The Z-axis represents coordinate values in a direction perpendicular to the detection plane (the distance from the detection plane). The detection plane of the radiation detector 42 lies in a plane at which Z=0. As shown in FIG. 6A, the radiation applying unit 24 is moved and the radiation is applied to four imaging targets OB1 to OB4 from three places. Of the four imaging targets, OB1 is the largest in size and OB4 is the smallest in size.

Figure 6B:
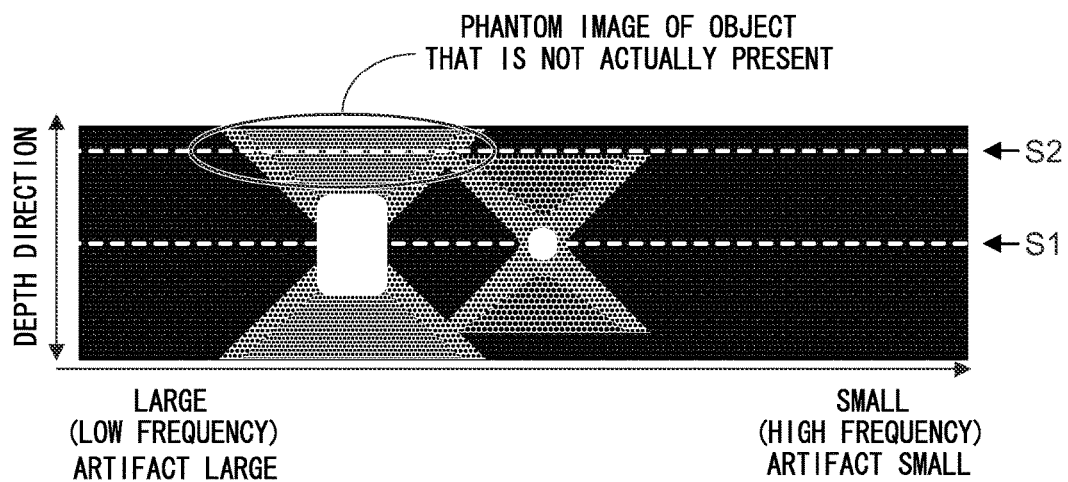
FIG. 6B is a cross-sectional view, parallel to the X-Z plane at position 150 in the Y-axis direction of FIG. 6A, when frequency processing has not been implemented on any of the projection images that have been captured and the tomographic images have been reconstructed and stacked in the Z-axis direction (depth direction) in correspondence to the slice positions of the tomographic images.
Figure 6C:
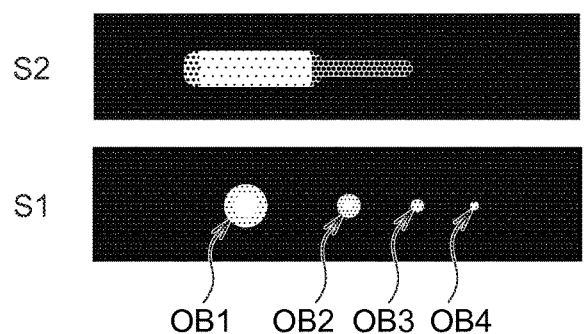
FIG. 6C shows tomographic images corresponding to slice positions S1 and S2 in FIG. 6B.

FIG. 6B is a cross-sectional view, parallel to the X-Z plane at Y-axis position 150, when the frequency processing has not been implemented on any of the projection images that have been captured and the tomographic images have been reconstructed and stacked in the depth direction in correspondence to the slice positions of the tomographic images (see also FIG. 6A). Furthermore, FIG. 6C shows tomographic images corresponding to slice positions S1 and S2 in FIG. 6B.

As shown in FIG. 6B, S1 corresponds to a position where OB1 is actually present, and an image of OB1 appears clearly in the tomographic image of S1. However, a phantom image (artifact) of object OB1 ends up appearing in the tomographic image of S2 even though S2 is a position where OB1 is not really present. Additionally, as will be apparent from FIG. 6B and FIG. 6C, the larger the size of the object is, the larger the phantom image becomes in the depth direction. Here, it will be understood that when images are converted to spatial frequency regions, the image of an object large in size is converted as the low-frequency component and the image of an object small (fine) in size is converted as the high-frequency component, and when images are represented in spatial frequency regions in this way, artifacts in the depth direction become larger in proportion to the low-frequency component object and artifacts in the depth direction become smaller in proportion to the high-frequency component object.

Figure 7:
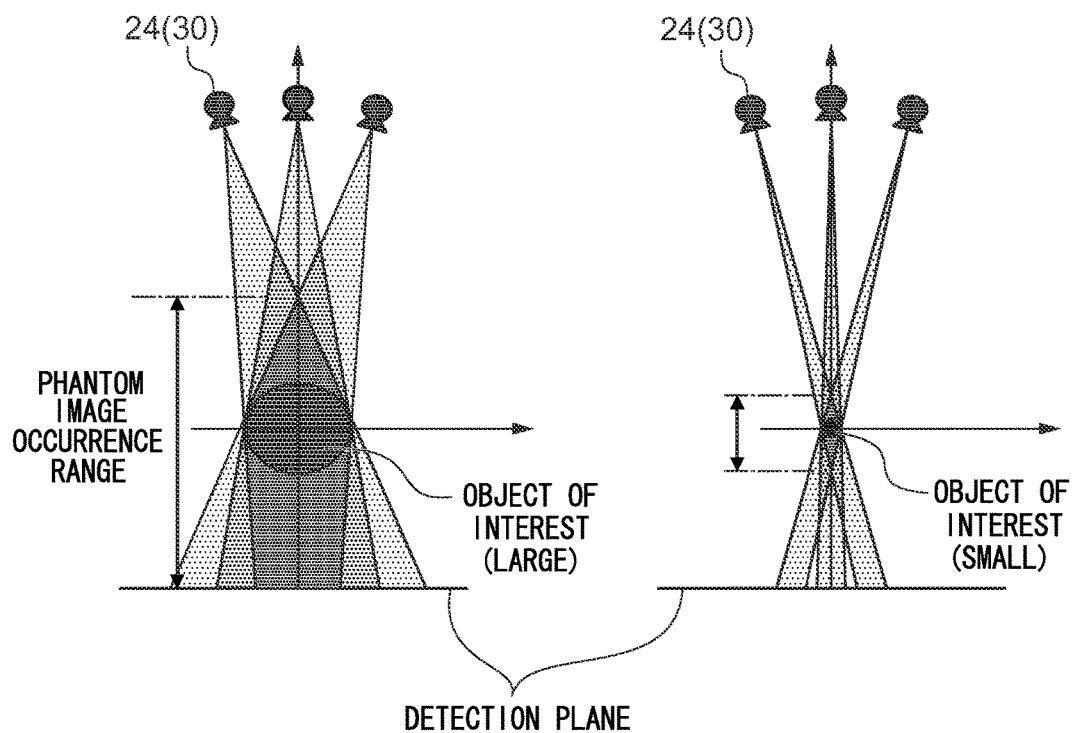
FIG. 7 is an explanatory drawing showing the reason why artifacts occur.

As shown in FIG. 7, the larger the size of the object is, the larger the area irradiated with radiation becomes, and when the radiation that has passed through the object is detected at the detection plane, the size of the object appearing in the projection images also becomes larger. Additionally, the larger the angle of incidence is, the more the object appears in a region away from the region where the object is actually present, and when the tomographic images reconstructed from the projection images are stacked together, artifacts in which the object seems stretched in the depth direction end up occurring in the range in which the regions where the radiation was applied lie on top of one another in the depth direction. The larger the object is, the larger the artifacts in the depth direction become.

In the FBP method, which is a representative CT reconstruction method, a filter is applied across the board to the plural projection images to correct them and then the images are reconstructed to thereby control artifacts. A case will be described where this is applied so that filtering is performed across the board on projection images obtained by tomosynthesis imaging.

Figure 8A:
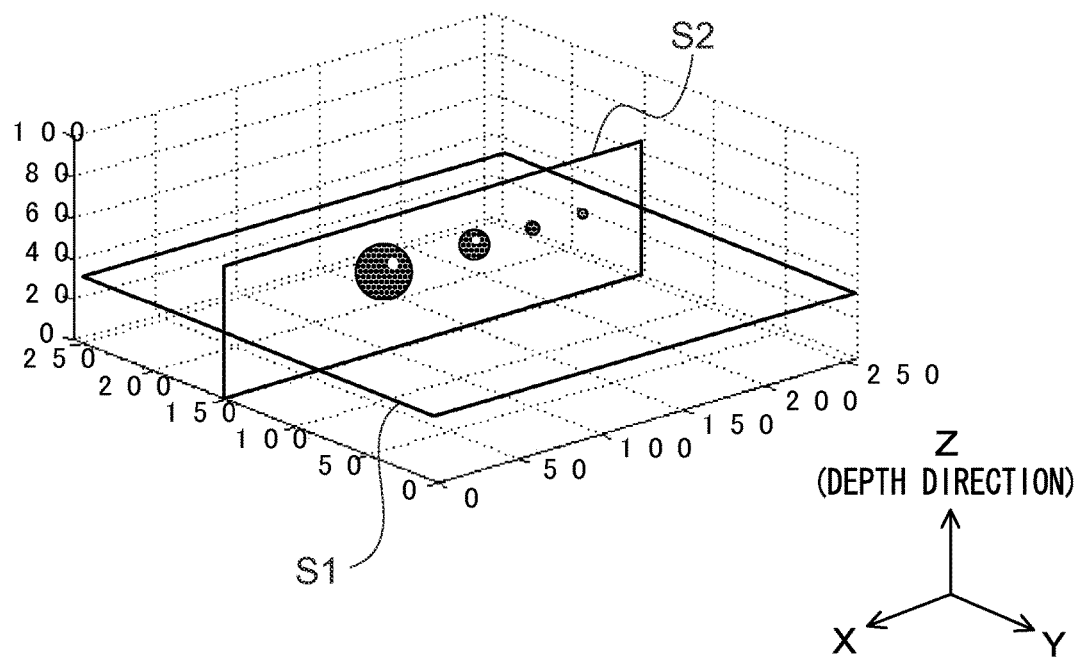
FIG. 8A is a drawing schematically showing the positions of the images shown in FIG. 8B.
Figure 8B:
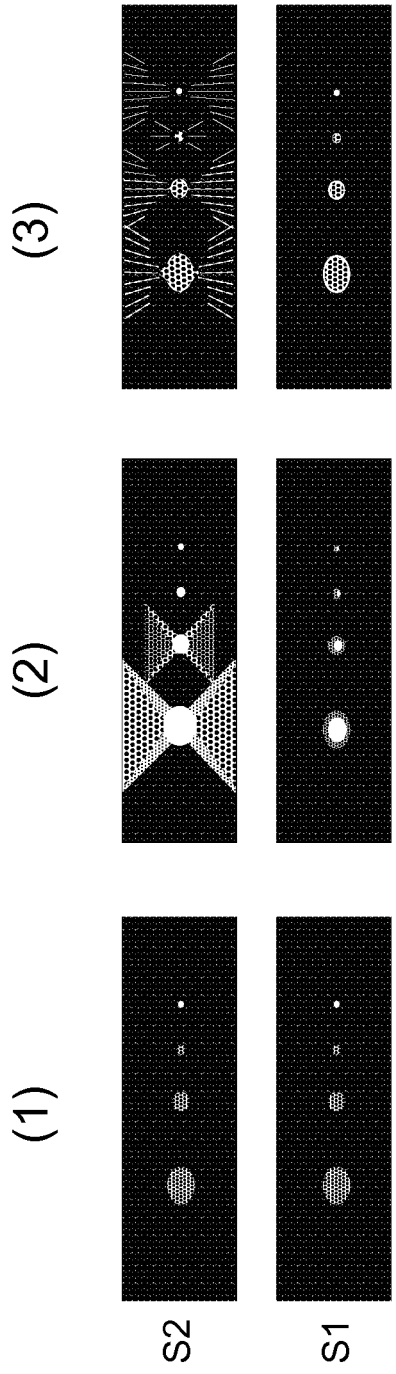
FIG. 8B is a drawing showing, according to types of frequency processing, combinations of tomographic images corresponding to position S1 parallel to the detection plane of a radiation detector at a position in the depth direction where object of interests are present and images corresponding to cross section S2 along the depth direction when the reconstructed tomographic images have been stacked in the depth direction in correspondence to their slice positions.

FIG. 8B shows combinations of tomographic images corresponding to position S1 parallel to the detection plane of the radiation detector 42 at a position in the depth direction where objects of interest are present and images corresponding to cross section S2 along the depth direction when the reconstructed tomographic images have been stacked in the depth direction in correspondence to their slice positions (see also FIG. 8A). Here, three patterns of combinations are shown from (1) to (3). (1) in FIG. 8B is a combination of ideal images that should really be projected. (2) is a combination of images when all the projection images have been filtered across the board by a low-pass filter (LPF) and reconstructed. (3) is a combination of images when all the projection images have been filtered by a high-pass filter (HPF) and reconstructed.

As shown in (2) of FIG. 8B, when the low-frequency component is extracted and the high-frequency component is attenuated across the board, artifacts occur in the depth direction. Furthermore, as mentioned above, the larger the object is, the larger the artifacts become.

As shown in (3) of FIG. 8B, when the high-frequency component is extracted and the low-frequency component is attenuated across the board, the artifacts become smaller (less conspicuous), but with the larger objects, just the outlines of the objects remain and the information of the low-frequency component of the object interiors—that is, density information—ends up disappearing. This is because just the sections in which the density varies a great extent are extracted by the HPF, and regions of the low-frequency component in which there are few variations in density end up disappearing without being extracted.

When reading a radiographic image of a breast using a mammography machine, the rough structures of fat, mammary glands, lesions (masses), and mammary glands, which are considered the main targets (objects of interest) of reading, can to a certain extent be classified into low-frequency components large in size. Consequently, in the present embodiment, across-the-board frequency processing is not performed on all the projection images; rather, by performing frequency processing that attenuates, relative to the high-frequency component, the low-frequency component of the projection images in which the angle of incidence is equal to or greater than the first threshold, artifacts in tomographic images in which an object of interest is not really present are made less conspicuous while controlling an extreme drop in the image density of the object of interest.

Figure 9A:
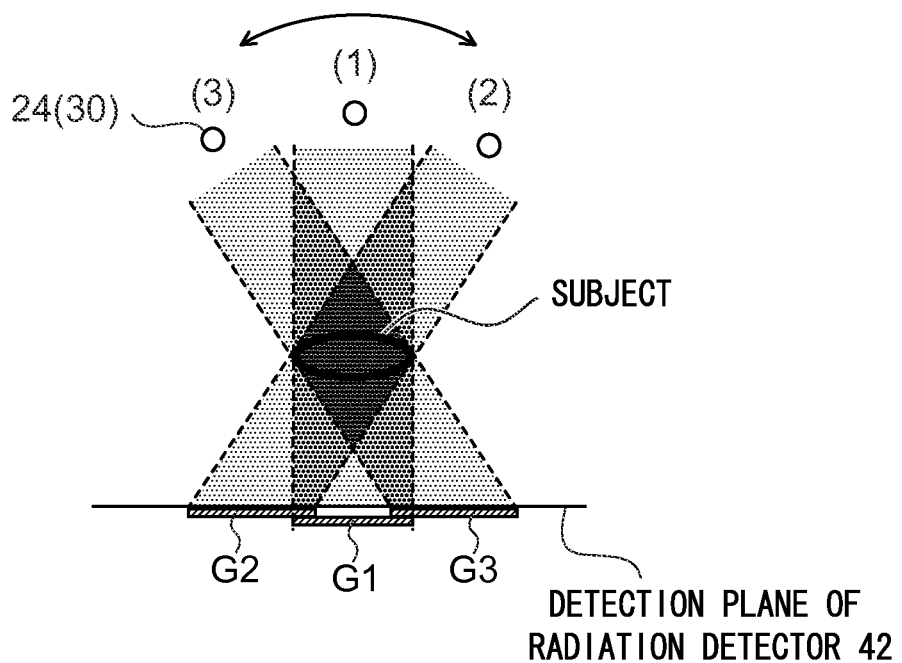
FIG. 9A is an explanatory drawing describing a case where frequency processing is not performed.

This principle will be described with reference to the schematic drawings of FIG. 9A and FIG. 9B. FIG. 9A is an explanatory drawing describing a case where frequency processing is not performed on each of the projection images, and FIG. 9B is an explanatory drawing describing a case where the low-frequency component attenuation processing is performed on the projection images in which the angle of incidence is large.

Figure 9B:
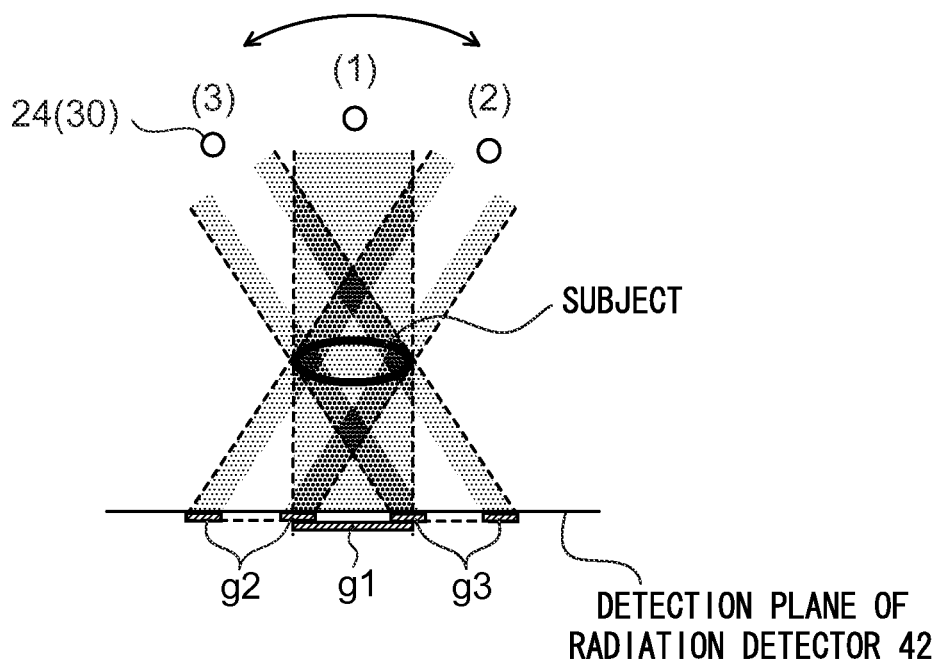
FIG. 9B is an explanatory drawing describing a case where frequency processing that attenuates the low-frequency component is performed on projection images in which the angle of incidence is large.

Both FIG. 9A and FIG. 9B show the radiation applying unit 24 being moved and radiation being applied toward the subject from the three places of (1), (2), and (3) to capture three projection images. (1) is a position at which the angle of incidence is 0 and (2) and (3) are positions at which the angle of incidence is equal to or greater than the first threshold. Sections where the multiple application ranges of the radiation applied from the different directions coincide are depicted in such a way that the density becomes higher in accordance with the state of coincidence. Although cone beam radiation is applied in actual tomosynthesis imaging, here, parallel radiation beams are depicted as being applied from each position in order to facilitate understanding of the frequency processing.

As shown in FIG. 9A, when radiation is applied from the position of (1) to the subject, the subject image is projected on the area of G1 of the projection image. When radiation is applied from the position of (2) to the subject, the subject image is projected on the area of G2 of the projection image. When radiation is applied from the position of (3) to the subject, the subject image is projected onto the area of G3 of the projection image. Consequently, when tomographic images corresponding to slice positions in which the subject is not really present are reconstructed, phantom images end up occurring because of G2 and G3.

In contrast, as shown in FIG. 9B, when radiation is applied from the position of (2) to the subject and the frequency processing that attenuates the low-frequency component is performed on the captured projection image, the projection range of the subject image is limited to the area of g2. In the same way, when radiation is applied from the position of (3) to the subject and the frequency processing that attenuates the low-frequency component is performed on the captured projection image, the projection range of the subject image is limited to the area of g3. That is, compared to G2 and G3 in FIG. 9A, just the outline sections of the images of the subject remain and the density on the inside is attenuated. Consequently, even when tomographic images corresponding to slice positions in which the subject is not really present are reconstructed from these projection images, the density of the phantom images becomes lower because of the attenuation of the low-frequency component. The low-frequency component attenuation processing is not performed (the degree of attenuation is set to 0) on the projection image captured as a result of applying the radiation from the position of (1) to the subject, so an extreme drop in the density of the subject is controlled in the tomographic images that are reconstructed.

Although an example where the frequency processing unit 66 performs processing that attenuates the low-frequency component without performing processing that enhances the high-frequency component has been described here as an example of the frequency processing that attenuates, relative to the high-frequency component, the low-frequency component, the frequency processing is not limited to this. As the frequency processing, for example, the frequency processing unit 66 may also perform processing that enhances the high-frequency component (hereinafter called high-frequency component enhancement processing) without performing processing that attenuates the low-frequency component. Furthermore, as the frequency processing, the frequency processing unit 66 may also be configured to perform both processing that attenuates the low-frequency component and processing that enhances the high-frequency component. Furthermore, for example, the frequency processing unit 66 may also perform processing that attenuates both the low-frequency component and the high-frequency component, and in that case the frequency processing unit 66 may perform the processing with the degree of attenuation of the low-frequency component being set to D1 and the degree of attenuation of the high-frequency component being set to D2, which is smaller than D1. Furthermore, for example, the frequency processing unit 66 may also perform processing that enhances both the low-frequency component and the high-frequency component, and in that case the frequency processing unit 66 may perform the processing with the degree of enhancement of the low-frequency component being set to D3 and the degree of enhancement of the high-frequency component being set to D4, which is larger than D3.

Furthermore, here, the frequency processing unit 66 implements frequency processing that relatively attenuates the low-frequency component with respect to the projection images in which the angle of incidence is equal to or greater than the first threshold, but the first threshold can be set beforehand in accordance with the moving distance of the radiation applying unit 24 (the radiation source 30), for example. Furthermore, the frequency processing unit 66 may also be configured to implement frequency processing that attenuates the low-frequency component with respect to each of the projection images other than the projection image in which the angle of incidence is the smallest. In this case, assuming that, of the angles of incidence at the time when the plural projection images are captured, a1 denotes the smallest angle of incidence and a2 denotes the second smallest angle of incidence, the first threshold can be set in a range greater than a1 and equal to or less than a2. Because the positions of the radiation source 30 during tomosynthesis imaging are set beforehand, instead of setting the value of the first threshold, the positions of the radiation source 30 at which the angle of incidence is equal to or greater than the first threshold among the multiple positions of the radiation source 30 during tomosynthesis imaging may also be set. It suffices for the frequency processing unit 66 to implement processing that attenuates the low-frequency component on the projection images that have been obtained by applying radiation from set positions.

Next, in step 104, the CPU 52 controls the tomographic image generating unit 68 to reconstruct tomographic images from the plural projection images. The projection images used for the reconstruction are the projection images in which the angle of incidence is less than the first threshold and the projection images in which the angle of incidence is equal to or greater than the first threshold and on which the frequency processing that attenuates the low-frequency component has been performed. The method of reconstruction is not particularly limited.

In step 106, the CPU 52 outputs (e.g., outputs to the image display instructing unit 62) the sets of image information of the reconstructed tomographic images.

As described above, in the radiographic imaging system 5 of the present embodiment, the radiographic imaging machine 10 captures plural projection images by tomosynthesis imaging. The image processing device 50 acquires the plural projection images that have been captured and stores them in the storage unit 74. The image processing device 50 of the present embodiment executes, with respect to the acquired projection images, frequency processing according to the angles of incidence, reconstructs the plural tomographic images, and outputs the reconstructed tomographic images.

In this way, control of artifacts and control of a drop in image density can be realized in a balanced manner compared to a case where frequency processing is performed across the board with respect to the projection images used in the reconstruction of the tomographic images.

The action of the image processing device 50 is not limited to what is described above.

For example, the frequency processing unit 66, when performing the frequency processing, may also be configured to increase the degree to which it relatively attenuates the low-frequency component as the angle of incidence becomes larger. For example, when performing the low-frequency component attenuation processing, the frequency processing unit 66 may be configured to increase the degree to which it attenuates the low-frequency component as the angle of incidence becomes larger. Furthermore, for example, when performing the high-frequency component enhancement processing on the projection images in which the angle of incidence is equal to or greater than the first threshold, the frequency processing unit 66 may be configured to increase the degree to which it enhances the high-frequency component as the angle of incidence becomes larger. Because of this, control of artifacts and control of a drop in the image density of an object of interest included in the tomographic images reconstructed from the plural projection images obtained by tomosynthesis imaging can be realized in a more balanced manner.

Moreover, as the frequency processing according to the angles of incidence performed by the frequency processing unit 66, instead of the processing exemplified above, the frequency processing unit 66 may also be configured to perform frequency processing that enhances, relative to the high-frequency component, the low-frequency component of the projection images in which the angle of incidence is less than a second threshold. For example, the frequency processing unit 66 can also perform, with respect to the projection images in which the angle of incidence is less than the second threshold, frequency processing that does not attenuate the high-frequency component but enhances the low-frequency component, or frequency processing that does not enhance the low-frequency component but attenuates the high-frequency component, or frequency processing that enhances the low-frequency component and attenuates the high-frequency component. Because of this, a drop in the density of an object of interest relative to the density of an artifact can be further controlled. The second threshold may be equal to the first threshold or different from the first threshold (e.g., smaller than the first threshold).

Furthermore, the frequency processing unit 66, when performing the frequency processing that relatively enhances the low-frequency component of the projection images in which the angle of incidence is less than the second threshold, may also be configured to increase the degree to which it relatively enhances the low-frequency component as the angle of incidence becomes smaller.

Moreover, during the reconstruction, the tomographic image generating unit 68 may be configured to apply to the projection images a weighting according to the angle of incidence and perform the reconstruction. For example, the tomographic image generating unit 68 may be configured to make the weighting it applies to the projection images in which the angle of incidence is equal to or greater than the first threshold smaller than the weighting it applies to the projection images in which the angle of incidence is less than the first threshold and perform the reconstruction. Because of this, artifacts become even less conspicuous. Furthermore, the tomographic image generating unit 68 may be configured to apply a smaller weighting the larger the angle of incidence is in the projection image and perform the reconstruction.

The method of the frequency processing performed by the frequency processing unit 66 is not particularly limited. For example, the frequency processing unit 66 may be configured to perform the frequency processing by performing convolution integration using a filter in which weighting factors are one-dimensionally or two-dimensionally arranged.

Furthermore, the frequency processing unit 66 may also be configured to perform the frequency processing by transforming the images onto a high-frequency space using the Fourier transform, applying a weighting to each low-frequency component so that the low-frequency component is attenuated relative to the high-frequency component in regard to the projection images in which the angle of incidence is equal to or greater than the first threshold, adding them together, and performing the inverse Fourier transform to return the images to the actual spatial regions.

Furthermore, for example, the multi-resolution decomposition method described in JP-A No. H06-301766 may also be used. Specifically, an image in which a specific frequency component is attenuated or enhanced can be formed by performing smoothing, converting an image into images of plural resolutions, finding the difference images between the images of each resolution, applying a weighting factor to the difference images, and integrating the difference images.

When performing the frequency processing using the Fourier transform or multi-resolution decomposition to decompose an image into plural frequency components, it is best to adjust the balance of the weighting of each frequency component and perform processing so that artifacts and fluctuations in the density of the image are controlled. In this way, because the balance of the weighting can be freely (nonlinearly) adjusted, frequency processing performed by decomposing an image into plural frequency components can also be called nonlinear filtering.

Furthermore, the frequency processing unit 66 may also implement frequency processing with an enhancement factor dependent on contrast. Specifically, when implementing nonlinear filtering, the frequency processing unit 66 can judge the level of contrast of each frequency band and change the weighting of each frequency component in accordance with the level of the contrast. Furthermore, for example, in a case where an object with high contrast (e.g., a high absorption object such as a man-made object or a calcification) is present, the frequency processing unit 66 may be configured to control the enhancement degree of the high-frequency component to thereby control artifacts caused by over-enhancement. Furthermore, in a case where an object with low contrast is present, such as an ordinary mammary gland or a mass, the frequency processing unit 66 may be configured to not just attenuate the low-frequency component but actively enhance the high-frequency component to make that object easier to see. By performing the frequency processing dependent on contrast in this way, tomographic images that make diagnosis easier can be reconstructed.

Furthermore, the frequency processing unit 66 may also, without disposing the first threshold and the second threshold, perform frequency processing that increases the degree as the angle of incidence becomes larger and attenuates, relative to the high-frequency component, the low-frequency component in the spatial frequency of the projection images.

Next, a case where the two-dimensional image generating unit 70 is activated by an instruction from the user, the tomographic images are reconstructed, and thereafter two-dimensional images are generated from the tomographic images will be described.

FIG. 10 is a flowchart showing a flow of a tomographic image and two-dimensional image generation processing program executed by the CPU 52 of the image processing device 50 of the present embodiment.

Step 100 to step 106 are the same as step 100 to step 106 of the tomographic image generation processing that was described above with reference to FIG. 5, so description thereof will be omitted here.

In step 108, the CPU 52 controls the two-dimensional image generating unit 70 to generate two-dimensional images from the reconstructed tomographic images.

In step 110, the CPU 52 outputs (e.g., outputs to the image display instructing unit 62) the sets of image information of the generated two-dimensional images and ends the tomographic image and two-dimensional image generation processing program.

Figure 11:
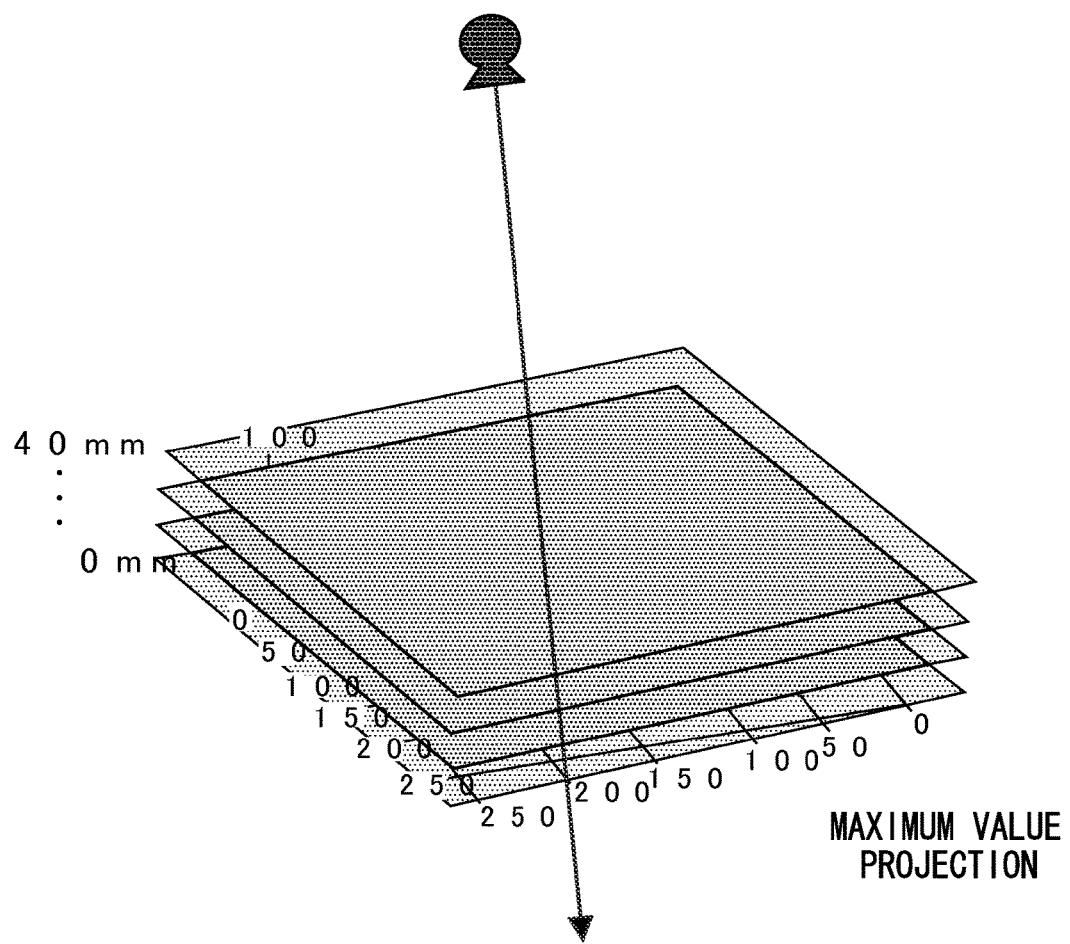
FIG. 11 is a schematic drawing describing maximum value projection processing.

As shown in FIG. 11, first, the two-dimensional image generating unit 70 performs projection processing along an arbitrary viewpoint direction with respect to stacked images in which the plural tomographic images generated by the tomographic image generating unit 68 have been stacked and selects the maximum pixel value (luminance value) in the projection path. The two-dimensional image generating unit 70 performs this processing for each pixel to generate two-dimensional images. Alternatively, the two-dimensional image generating unit 70 may also select the smallest pixel value in the projection path and generate two-dimensional images. Furthermore, the two-dimensional image generating unit 70 may also be configured to generate two-dimensional images by performing add processing that adds together the pixel values of corresponding pixels of the tomographic images along an arbitrary direction. Furthermore, the two-dimensional image generating unit 70 may also employ the two-dimensional image generating method described in U.S. Patent Application Publication No. 2010/135558 (A1). In this way, the two-dimensional image generating method is not particularly limited, and commonly known methods may be used.

Figure 12:
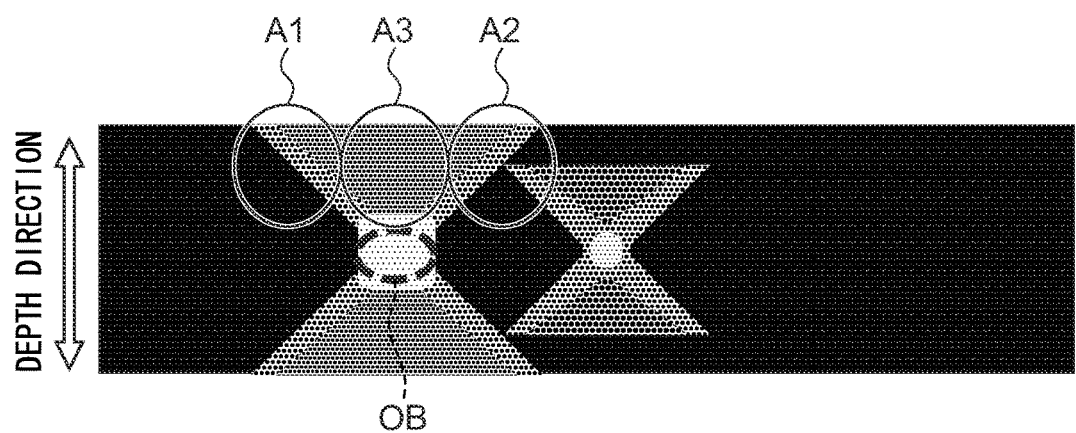
FIG. 12 is an explanatory drawing for describing artifacts and their effects on a two-dimensional image.

In this connection, because the two-dimensional image generating unit 70 generates two-dimensional images from the reconstructed tomographic images in this way, sometimes, depending on the artifacts occurring in the tomographic images, the effect of the artifacts also extends to the two-dimensional images generated from the tomographic images so that image blur ends up occurring. FIG. 12 is an example of a cross-sectional view of stacked images in which tomographic images have been stacked, and when OB denotes a region in which an object of interest is actually present, if artifacts appear in diagonal directions of the region OB like A1 and A2 in FIG. 12, for example, these artifacts end up causing image blur of the two-dimensional image.

However, by performing the frequency processing that attenuates, relative to the high-frequency component, the low-frequency component with respect to the projection images in which the angle of incidence is equal to or greater than the first threshold and reconstructing the tomographic images as described in the embodiment, tomographic images in which the artifacts are less conspicuous are generated, so the two-dimensional images generated from the tomographic images also become images in which the artifacts are less conspicuous.

Although a drop in the image density of an object of interest is controlled by implementing processing that relatively attenuates the low-frequency component with respect to the tomographic images in which the angle of incidence is less than the first threshold, because of this, as shown in A3 of FIG. 12 for example, sometimes a little artifact remains in the region (the region in the direction directly above OB) corresponding to the region OB at slice positions where the object of interest is not really present. However, because the two-dimensional images are generated by add processing or projection processing, the artifact exemplified in A3 of FIG. 12 has a smaller effect on image blur of the two-dimensional images than the artifacts exemplified in A1 and A2 of FIG. 12.

When performing add processing to generate the two-dimensional image, the two-dimensional image generating unit 70 may also perform the processing while achieving a balance in combination so that the variations in the density of the entire image do not deviate from the actual density, by, for example, making the weighting of the tomographic images corresponding to the slice positions in which the object of interest is present larger than the weighting of the other tomographic images.

Although an example where the two-dimensional image generating unit 70 is operated or not operated by an instruction from the user has been described in the above embodiment, the image processing device 50 is not limited to this. The image processing device 50 may also be configured in such a way that the two-dimensional image generating unit 70 is always operated to generate two-dimensional images regardless of an instruction from the user, or conversely the image processing device 50 can also be given a configuration in which the two-dimensional image generating unit 70 is not disposed.

Furthermore, in the present embodiment, the frequency processing is performed with respect to the projection images stored in the storage unit 74 of the image processing device 50 to generate the tomographic images, but the present disclosure is not limited to this, and the frequency processing may also be performed with respect to projection images received from the outside via the network 49 to generate the tomographic images.

Furthermore, in the present embodiment, a case where the image processing device is applied to the generation of tomographic images of projection images captured by a mammography machine has been described, but the present disclosure is not limited to this. For example, the image processing device may also be applied to the generation of tomographic images of projection images captured by another radiographic imaging machine such as a so-called C-arm radiographic imaging machine that rotates with the positional relationship between the radiation source and the radiation detector remaining fixed.

Furthermore, the radiation used in the tomosynthesis imaging is not particularly limited, and X-rays and γ rays can be applied.

In addition, the configurations of the radiographic imaging system 5, the radiographic imaging machine 10, the image processing device 50, and the display device 80 described in the present embodiment are examples and, needless to say, can be changed in accordance with the situation without departing from the spirit of the present disclosure.

Furthermore, in the present embodiment, an example where the frequency processing unit 66, the tomographic image generating unit 68, and the two-dimensional image generating unit 70 are each realized by hardware (e.g., hardware configured by a common electronic circuit, ASIC, or FPGA) has been described, but they may also be functions realized as a result of the CPU 52 executing programs.

Furthermore, the flow of the tomographic image generation processing described in the present embodiment is also an example and, needless to say, can be changed in accordance with the situation without departing from the spirit of the present disclosure.

In the technology described in JP-A No. 2005-152658, the weighting factors are assigned on the basis of the number of times that the pixels at each slice position are traversed by radiation the radiation source position, the relative height from the detector plane, and the distance from the subject, and although it is possible to control artifacts in parts where the subject thickness is thin, for example, the situation unique to tomosynthesis imaging described above cannot be resolved. Furthermore, although the technology described in JP-A No. 2005-7061 performs correction processing with respect to an image obtained by two-dimensional imaging, this technology cannot resolve the artifact situation unique to tomosynthesis imaging.

The present disclosure provides image processing devices, a radiographic imaging system, image processing methods, and image processing programs which, when reconstructing tomographic images from projection images that have been obtained by tomosynthesis imaging, can make artifacts in the tomographic images at slice positions where an object of interest is not actually present less conspicuous while controlling a significant drop in the density of the object of interest.

An image processing device pertaining to a first disclosure comprises: an acquiring section that acquires a plurality of projection images in which a subject between a radiation detector and a radiation applying unit has, as a result of the radiation applying unit being moved to thereby change the angle of incidence, with respect to the subject, of radiation applied from the radiation applying unit, been captured at each different angle of incidence; a processing section that performs frequency processing that attenuates, relative to a high-frequency component, a low-frequency component of the projection images in which the angle of incidence is equal to or greater than a first threshold; and a tomographic image generating section that generates tomographic images of the subject by reconstructing them from the projection images in which the angle of incidence is less than the first threshold and the frequency-processed projection images.

In this way, by performing the frequency processing that attenuates, relative to the high-frequency component, the low-frequency component of the projection images in which the angle of incidence is equal to or greater than the first threshold and reconstructing the tomographic images, the low-frequency component of the projection images in which the angle of incidence is equal to or greater than the first threshold can be attenuated relative to the high-frequency component without attenuating, relative to the high-frequency component, the low-frequency component of the projection images in which the angle of incidence is less than the first threshold, and artifacts in tomographic images at slice positions where an object of interest is not actually present can be made less conspicuous while controlling an extreme drop in the density of the object of interest.

The present disclosure may also be configured in such a way that the processing section performs, as the frequency processing, at least one of processing that attenuates the low-frequency component of the projection images in which the angle of incidence is equal to or greater than the first threshold and processing that enhances the high-frequency component of the projection images in which the angle of incidence is equal to or greater than the first threshold.

Furthermore, the present disclosure may also be configured in such a way that the processing section, when performing the frequency processing that relatively attenuates the low-frequency component, increases the degree to which it relatively attenuates the low-frequency component as the angle of incidence becomes larger.

Furthermore, the present disclosure may also be configured in such a way that the tomographic image generating section applies a weighting according to the angle of incidence to the projection images in which the angle of incidence is less than the first threshold and the projection images on which the frequency processing has been performed and reconstructs the tomographic images.

For example, the weighting applied to the projection images in which the angle of incidence is equal to or greater than the first threshold may be made smaller than the weighting applied to the projection images in which the angle of incidence is less than the first threshold. Furthermore, the weighting applied to the projection images may be made smaller as the angle of incidence becomes larger. Because of this, artifacts can be made even less conspicuous.

Furthermore, the present disclosure may also be configured in such a way that the processing section further performs frequency processing that enhances, relative to the high-frequency component, the low-frequency component of the projection images in which the angle of incidence is less than a second threshold.

In particular, the present disclosure may be configured in such a way that the processing section, when performing the frequency processing that relatively enhances the low-frequency component, increases the degree to which it relatively enhances the low-frequency component as the angle of incidence becomes smaller.

An image processing device pertaining to a second disclosure comprises: an acquiring section that acquires a plurality of projection images in which a subject between a radiation detector and a radiation applying unit has, as a result of the radiation applying unit being moved to thereby change the angle of incidence, with respect to the subject, of radiation applied from the radiation applying unit, been captured at each different angle of incidence; a processing section that performs frequency processing that increases the degree as the angle of incidence becomes larger and which attenuates, relative to a high-frequency component, a low-frequency component of the projection images; and a tomographic image generating section that generates tomographic images of the subject by reconstructing them from the projection images on which the frequency processing has been performed by the processing section.

In this way, by performing the frequency processing that increases the degree as the angle of incidence becomes larger and attenuates, relative to the high-frequency component, the low-frequency component of the projection images and reconstructing the tomographic images, artifacts in tomographic images at slice positions where an object of interest is not actually present can be made less conspicuous while controlling an extreme drop in the density of the object of interest.

Furthermore, the present disclosure may further comprise a two-dimensional image generating section that generates a two-dimensional image by performing projection processing along a predetermined direction or performing add processing that adds pixel values of corresponding pixels along a predetermined direction with respect to stacked images in which the plurality of tomographic images generated by the tomographic image generating section are stacked.

A radiographic imaging system pertaining to a third disclosure comprises: a radiographic imaging machine that is equipped with a radiation detection and a radiation applying unit and, after moving the radiation applying unit to thereby change the angle of incidence, with respect to a subject between the radiation detector and the radiation applying unit, of radiation applied from the radiation applying unit, applies the radiation to the subject to thereby capture a plurality of projection images at each different angle of incidence; and the aforementioned image processing device, which generates tomographic images from the plurality of projection images captured by the radiographic imaging machine.

Furthermore, an image processing program pertaining to a fourth disclosure is a program for causing a computer to function as: an acquiring section that acquires a plurality of projection images in which a subject between a radiation detector and a radiation applying unit has, as a result of the radiation applying unit being moved to thereby change the angle of incidence, with respect to the subject, of radiation applied from the radiation applying unit, been captured at each different angle of incidence; a processing section that performs frequency processing that attenuates, relative to a high-frequency component, a low-frequency component of the projection images in which the angle of incidence is equal to or greater than a first threshold; and a tomographic image generating section that generates tomographic images of the subject by reconstructing them from the projection images in which the angle of incidence is less than the first threshold and the frequency-processed projection images.

Furthermore, an image processing program pertaining to a fifth disclosure is a program for causing a computer to function as: an acquiring section that acquires a plurality of projection images in which a subject between a radiation detector and a radiation applying unit has, as a result of the radiation applying unit being moved to thereby change the angle of incidence, with respect to the subject, of radiation applied from the radiation applying unit, been captured at each different angle of incidence; a processing section that performs frequency processing that increases the degree as the angle of incidence becomes larger and which attenuates, relative to a high-frequency component, a low-frequency component of the projection images; and a tomographic image generating section that generates tomographic images of the subject by reconstructing them from the projection images on which the frequency processing has been performed by the processing section.

Furthermore, an image processing method pertaining to a sixth disclosure comprises: acquiring a plurality of projection images in which a subject between a radiation detector and a radiation applying unit has, as a result of the radiation applying unit being moved to thereby change the angle of incidence, with respect to the subject, of radiation applied from the radiation applying unit, been captured at each different angle of incidence; performing frequency processing that attenuates, relative to a high-frequency component, a low-frequency component of the projection images in which the angle of incidence is equal to or greater than a first threshold; and generating tomographic images of the subject by reconstructing them from the projection images in which the angle of incidence is less than the first threshold and the frequency-processed projection images.

Moreover, an image processing method pertaining to a seventh disclosure comprises: acquiring a plurality of projection images in which a subject between a radiation detector and a radiation applying unit has, as a result of the radiation applying unit being moved to thereby change the angle of incidence, with respect to the subject, of radiation applied from the radiation applying unit, been captured at each different angle of incidence; performing frequency processing that increases the degree as the angle of incidence becomes larger and which attenuates, relative to a high-frequency component, a low-frequency component of the projection images; and generating tomographic images of the subject by reconstructing them from the projection images on which the frequency processing has been performed.

The radiographic imaging system, the image processing programs, and the image processing methods also act in the same way as the above-described image processing devices, so artifacts in tomographic images at slice positions where an object of interest is not actually present can be made less conspicuous while controlling an extreme drop in the density of the object of interest.

ADVANTAGEOUS EFFECTS OF INVENTION

As described above, artifacts in tomographic images at slice positions where an object of interest is not actually present can be made less conspicuous while controlling an extreme drop in the density of the object of interest.

The disclosures of Japanese Patent Application No. 2012-273734 and Japanese Patent Application No. 2013-242257 are incorporated in their entireties by reference herein. All publications, patent applications, and technical standards mentioned in this specification are incorporated by reference herein to the same extent as if each individual publication, patent application, or technical standard was specifically and individually indicated to be incorporated by reference.

The invention claimed is:

1. An image processing device, comprising:
   an acquiring section that acquires a plurality of projection images in which a subject between a radiation detector and a radiation applying unit has, as a result of the radiation applying unit being moved to thereby change an angle of incidence, with respect to the subject, of radiation applied from the radiation applying unit, been imaged at each different angle of incidence;
   a processing section that performs frequency processing that attenuates, relative to a high-frequency component, a low-frequency component of projection images in which the angle of incidence is equal to or greater than a first threshold; and
   a tomographic image generating section that generates tomographic images of the subject by image reconstruction from projection images in which the angle of incidence is less than the first threshold and from the frequency-processed projection images.

2. The image processing device according to claim 1, wherein the processing section performs, as the frequency processing, at least one of processing that attenuates the low-frequency component of the projection images in which the angle of incidence is equal to or greater than the first threshold or processing that enhances the high-frequency component of the projection images in which the angle of incidence is equal to or greater than the first threshold.

3. The image processing device according to claim 1, wherein the processing section, when performing the frequency processing that relatively attenuates the low-frequency component, increases the degree of relative attenuation of the low-frequency component as the angle of incidence becomes larger.

4. The image processing device according to claim 1, wherein the tomographic image generating section applies a weighting, according to the angle of incidence, to the projection images in which the angle of incidence is less than the first threshold and to the projection images on which the frequency processing has been performed, and reconstructs the tomographic images.

5. The image processing device according to claim 1, wherein the processing section further performs frequency processing that enhances, relative to the high-frequency component, the low-frequency component of projection images in which the angle of incidence is less than a second threshold.

6. The image processing device according to claim 5, wherein the processing section, when performing the frequency processing that relatively enhances the low-frequency component, increases the degree of relative enhancement of the low-frequency component as the angle of incidence becomes smaller.

7. The image processing device according to claim 1, further comprising a two-dimensional image generating section that generates a two-dimensional image by performing projection processing along a predetermined direction or performing addition processing that adds pixel values of corresponding pixels along a predetermined direction with respect to stacked images in which a plurality of the tomographic images generated by the tomographic image generating section are stacked.

8. A radiographic imaging system, comprising:
   a radiographic imaging device that is equipped with a radiation detector and a radiation applying unit and that, while moving the radiation applying unit to thereby change an angle of incidence, with respect to a subject between the radiation detector and the radiation applying unit, of radiation applied from the radiation applying unit, applies the radiation to the subject to thereby capture a plurality of projection images at each different angle of incidence; and
   the image processing device according to claim 1, which generates tomographic images from the plurality of projection images captured by the radiographic imaging machine.

9. A non-transitory recording medium storing an image processing program for causing a computer to function as:
   an acquiring section that acquires a plurality of projection images in which a subject between a radiation detector and a radiation applying unit has, as a result of the radiation applying unit being moved to thereby change an angle of incidence, with respect to the subject, of radiation applied from the radiation applying unit, been imaged at each different angle of incidence;
   a processing section that performs frequency processing that attenuates, relative to a high-frequency component, a low-frequency component of projection images in which the angle of incidence is equal to or greater than a first threshold; and a tomographic image generating section that generates tomographic images of the subject by image reconstruction from projection images in which the angle of incidence is less than the first threshold and from the frequency-processed projection images.

10. An image processing method, comprising:

acquiring a plurality of projection images in which a subject between a radiation detector and a radiation applying unit has, as a result of the radiation applying unit being moved to thereby change an angle of incidence, with respect to the subject, of radiation applied from the radiation applying unit, been imaged at each different angle of incidence;

performing frequency processing that attenuates, relative to a high-frequency component, a low-frequency component of projection images in which the angle of incidence is equal to or greater than a first threshold; and generating tomographic images of the subject by image reconstruction from projection images in which the angle of incidence is less than the first threshold and from the frequency-processed projection images.

* * * * *